United States Patent [19]

Fürstenwerth

[11] Patent Number: 4,895,957

[45] Date of Patent: Jan. 23, 1990

[54] PROCESS FOR THE PREPARATION OF 4-SUBSTITUTED 3-METHYL-1-ARYL-5-AMINO-PYRAZOLES

[75] Inventor: Hauke Fürstenwerth, Leverkusen, Fed. Rep. of Germany

[73] Assignee: Bayer Aktiengesellschaft, Leverkusen, Fed. Rep. of Germany

[21] Appl. No.: 278,698

[22] Filed: Dec. 1, 1988

[30] Foreign Application Priority Data

Dec. 16, 1987 [DE] Fed. Rep. of Germany ....... 3742612

[51] Int. Cl.⁴ ............................................ C07D 231/44
[52] U.S. Cl. .................................................. 548/362
[58] Field of Search ......................................... 548/362

[56] References Cited

U.S. PATENT DOCUMENTS 4,614,533 9/1986 Schallner et al. .................... 548/362
4,771,066 9/1988 Gehring et al. ..................... 548/362

*Primary Examiner*—Robert W. Ramsuer
*Attorney, Agent, or Firm*—Sprung Horn Kramer & Woods

[57] ABSTRACT

A process for the preparation of a 4-substituted 3-methyl-1-aryl-5-amino-pyrazole of the formula

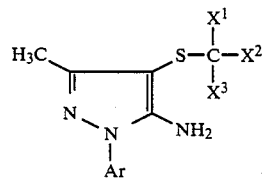

in which
  $X^1$, $X^2$ and $X^3$ independently of one another each stand for halogen and
  Ar stands for optionally substituted phenyl.

20 Claims, No Drawings

PROCESS FOR THE PREPARATION OF 4-SUBSTITUTED 3-METHYL-1-ARYL-5-AMINO-PYRAZOLES

The invention relates to a new process for the preparation of known 4-substituted 3-methyl-1-aryl-5-amino-pyrazoles, which possess insecticidal properties.

It is already known that 4-substituted 3-alkyl-1-aryl-5-amino-pyrazoles are obtained when 4-unsubstituted 3-alkyl-1-aryl-5-amino-pyrazoles are reacted with electrophilic reagents (cf. EP No. 201,852). In this process, the 4-unsubstituted 3-alkyl-1-aryl-5-amino-pyrazoles used as precursors are generally prepared from suitably substituted acrylonitrile derivatives and corresponding arylhydrazines via several different intermediate steps to be isolated as intermediates (cf. EP No. 201,852).

The disadvantages of a multi-step reaction procedure are obvious, in particular when starting compounds which are poorly accessible and thus costly—as, in this case, suitably substituted arylhydrazines—have to be employed as early as in the first step.

Furthermore, it is known that certain 4-substituted 1-aryl-5-amino-pyrazoles are also obtained when corresponding arylhydrazines are cyclized directly with suitably substituted acrylonitrile derivatives under certain reaction conditions (cf. DE-OS (German Published Specification) No. 3,402,308).

However, this process is suitable only for certain substituents to be introduced in the 4-position, that is to say, it cannot be used for all purposes. Thus, for example, α-alkylthio- or α-halogenoalkylthio-substituted β-dimethyl-amino-acrylonitriles cannot be cyclized directly with arylhydrazines without partial decomposition of the starting materials and/or final products at the high temperatures required, in particular when the reactivity of the participating arylhydrazines is much reduced by several electronegative substituents. The use of α-alkylthio- or α-halogenoalkylthio-β-alkoxy-substituted acrylonitriles fails because these starting compounds can be prepared only with difficulty. The 4-alkylthio- and 4-halogenoalkylthio-5-amino-1-aryl-pyrazoles which have several, generally electronegative, substituents in the aryl moiety and are interesting in particular as insecticides and herbicides (cf. DE-OS (German Published Specification) No. 3,402,308 and EP No. 201,852) are therefore not accessible via this path in a satisfactory yield and purity.

It has now been found that 4-substituted 3-methyl-1-aryl-5-amino-pyrazoles of the general formula (I)

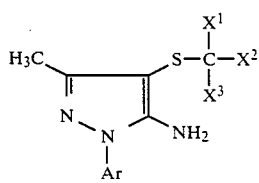

in which
X$^1$, X$^2$ and X$^3$ independently of one another each stand for halogen and
Ar stands for optionally substituted phenyl
are obtained when 3-ketobutyraldehyde dimethyl acetal of the formula (II)

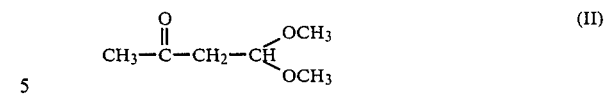

is first reacted with amines of the formula (III)

in which
R$^1$ and R$^2$ independently of one another each stand for hydrogen, alkyl, cycloalkyl or for in each case optionally substituted aralkyl, aryl or heteroaryl, or together with the nitrogen atom to which they are bonded stand for an optionally substituted heterocyclic ring which can optionally contain further hetero atoms,
if appropriate in the presence of a diluent, the reaction mixture is then further reacted directly without isolation of the intermediates of the formula (IV)

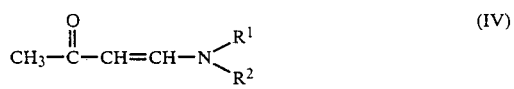

in which
R$^1$ and R$^2$ have the abovementioned meanings, with trihalogenomethanesulphenyl chlorides of the formula (V)

in which
X$^1$, X$^2$ and X$^3$ have the abovementioned meanings, if appropriate in the presence of a diluent and if appropriate in the presence of an acid-binding agent, the reaction mixtures are then further reacted directly, without isolation of the intermediates of the formula (VI)

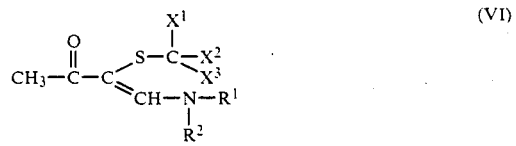

in which
R$^1$, R$^2$, X$^1$, X$^2$ and X$^3$ have the abovementioned meanings, with hydroxylamine hydrochloride in the presence of an acid-binding agent and if appropriate in the presence of a diluent, and the reaction mixture is then further reacted directly with arylhydrazines of the formula (IX)

in which
Ar has the abovementioned meaning, without isolation of the intermediates of the formula (VII)

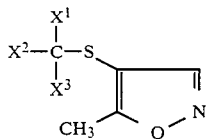

which, under the given reaction conditions, immediately react further to give the open-chain tautomers of the formula (VIIIa)

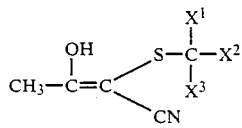

in which $X^1$, $X^2$ and $X^3$ have the abovementioned meanings, and of the formula (VIIIb)

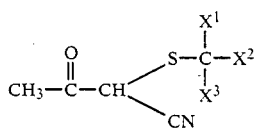

in which $X^1$, $X^2$ and $X^3$ have the abovementioned meanings, if appropriate in the presence of a diluent and in the presence of an acidic reaction auxiliary.

It must be considered as extremely surprising that the 5-step reaction according to the invention proceeds in the so-called "one-pot process" under mild conditions and in good yield, giving final products in high purity, since an integrated course of the reaction including all steps was not to be expected due to the polyfunctionality of the various starting materials employed.

Compared with the previously known multi-step preparation process, the process according to the invention has a series of advantages. Thus, the intended final products of the formula (I) are obtained in high yields and in a purity so high that, in general, additional, complex purification operations can be dispensed with. The one-step reaction procedure leading to considerable reductions of costly starting materials, auxiliaries and energy and waste water must be considered as a further advantage, which means a distinct improvement compared with the prior art, not only from the economical but also from the ecological points of view.

Formula (I) provides a general definition of the 4-substituted 3-methyl-1-aryl-5-amino-pyrazoles which can be prepared with the aid of the process according to the invention. Compounds of the formula (I) which can preferably be prepared are those in which $X^1$, $X^2$, $X^3$ independently of one another each stand for fluorine, chlorine, bromine or iodine and Ar stands for phenyl which is optionally monosubstituted or polysubstituted by identical or different substituents, suitable substituents in each case being: cyano, nitro, halogen, in each case straight-chain or branched alkyl, alkoxy or alkoxycarbonyl, each having 1 to 4 carbon atoms, in each case straight-chain or branched halogenoalkyl or halogenoalkoxy, each having 1 to 4 carbon atoms and 1 to 9 identical or different halogen atoms, or an $-S(O)_n-R^3$ radical, where $R^3$ stands for amino and for in each case straight-chain or branched alkyl, alkylamino, dialkylamino or halogenoalkyl, each having 1 to 4 carbon atoms in the individual alkyl moieties and, in the case of the halogenoalkyl, having 1 to 9 identical or different halogen atoms and n stands for a number 0, 1 or 2.

Compounds of the formula (I) which can particularly preferably be prepared are those in which $X_1$, $X^2$ and $X^3$ independently of one another each stand for fluorine, chlorine or bromine and Ar stands for phenyl which is optionally monosubstituted to pentasubstituted by identical or different substituents, suitable substituents in each case being: cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethox, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or an $-S(O)_n-R^3$ radical, where $R^3$ stands for amino, methylamino, ethylamino, dimethylamino, diethylamino, fluorodichloromethyl, difluoromethyl, tetrafluoroethyl, trifluorochloroethyl, trichloromethyl, trichloroethyl, triflfluoromethyl, methyl or ethyl, and n stands for a number 0, 1 or 2.

Compounds of the formula (I) which can very particularly preferably be prepared are those in which $X^1$, $X^2$ and $X^3$ independently of one another each stand for fluorine or chlorine and Ar stands for phenyl which is optionally monosubstituted to pentasubstituted by identical or different substituents, suitable substituents being: fluorine, chlorine, bromine, methyl, ethyl, methoxy, ethoxy, trifluoromethyl, trifluoromethoxy, trifluoromethylthio, trifluoromethylsulphinyl or trifluoromethylsulphonyl.

If, for example, 3-ketobutyraldehyde dimethyl acetal, dimethylamine, trifluoromethanesulfphenyl chloride and 2,6-dichloro-4-trifluoromethylphenylhydrazine are used as starting substances, the course of the reaction of the process according to the invention can be represented by the following equation:

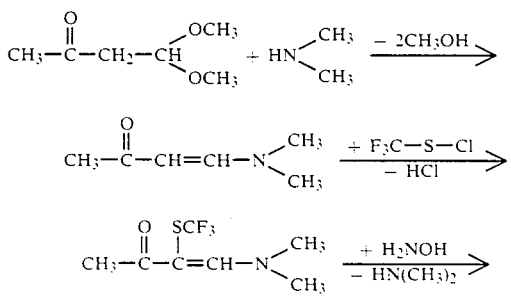

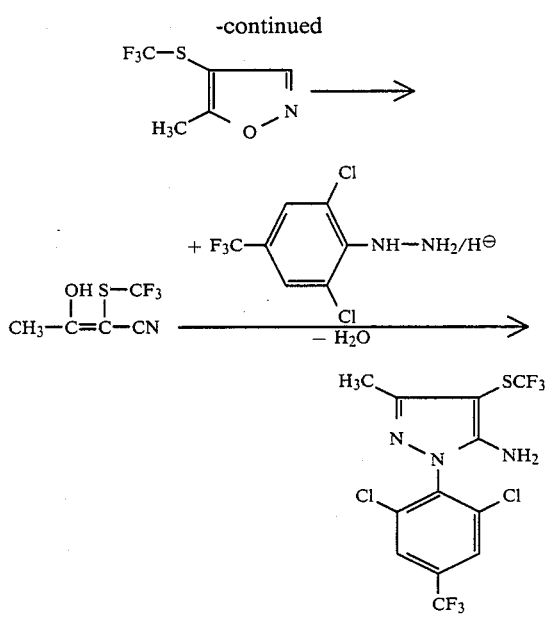

The 3-ketobutyraldehyde dimethyl acetal of the formula (II) which is required as starting compound for carrying out the process according to the invention is known (cf., for example, Chem. Ing. Tech. 46, 395 [1974] or J. org. Chem. 41, 3765 [1976]).

Formula (III) provides a general definition of the amines also required as starting substances for carrying out the process according to the invention. In this formula (III), $R^1$ and $R^2$ independently of one another preferably stand for hydrogen, straight-chain or branched alkyl having 1 to 4 carbon atoms, for cycloalkyl having 3 to 7 carbon atoms or for phenyl or benzyl, in each case optionally monosubstituted, disubstituted or trisubstituted by identical or different substituents, suitable substituents being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, trifluoromethylthio, methoxycarbonyl or ethoxycarbonyl, or $R^1$ and $R^2$ together with the nitrogen atom to which they are bonded stand for a five- or six-membered saturated heterocyclic ring which can optionally contain further hetero atoms, such as, in particular, nitrogen, oxygen or sulphur. Particularly preferably, $R^1$ and $R^2$ independently of one another stand for hydrogen, methyl, ethyl, n- or i-propyl, n-, i-, s- or t-butyl, cyclohexyl, phenyl or benzyl, or together with the nitrogen atom to which they are bonded stand for a 1-pyrrolidinyl radical, a 1-piperidinyl radical or a 4-morpholinyl radical.

The amines of the formula (III) are generally known compounds of organic chemistry.

Formula (V) provides a general definition of the trihalogenomethanesulphenyl chlorides also required as starting substances for carrying out the process according to the invention. In this formula (V), $X^1$, $X^2$ and $X^3$ preferably stand for those radicals which have already been mentioned in connection with the description of the substances of the formula (I) according to the invention as being preferred for these substituents.

The trihalogenomethanesulphenyl chlorides of the formula (V) are also generally known compounds of organic chemistry.

Formula (IX) provides a general definition of th arylhydrazines also required as starting substances for carrying out the process according to the invention. In this formula (IX), Ar preferably stands for those radicals which have already been mentioned in connection with the description of the substances of the formula (I) which can be prepared according to the invention as being preferred for these substituents.

The arylhydrazines of the formula (IX) are known or can be obtained in analogy to known processes (cf. for example EP No. 154,115 or EP No. 224,831 or EP No. 187,285 or EP No. 34,945).

Suitable diluents for carrying out the process according to the invention are inert organic solvents, or, if they are water-miscible, mixtures thereof with water or pure water. They include in particular aliphatic, alicyclic or aromatic optionally halogenated hydrocarbons, such as, for example, benzine, benzene, toluene, xylene, chlorobenzene, petroleum ether, hexane, cyclohexane, dichloromethane, chloroform, carbon tetrachloride; ethers, such as diethyl ether, dioxane, tetrahydrofuran or ethylene glycol dimethyl ether or ethylene glycol diethyl ether; amides, such as dimethylformamide, dimethylacetamide, N-methylformanilid, N-methylpyrrolidone or hexamethylphosphoric triamide; esters, such as ethyl acetate; sulphoxides or sulphones, such as dimethylsulphoxide or tetramethylenesulphone (sulpholane); alcohols, such as methanol, ethanol, propanol, butanol, ethylene glycol, the monomethyl or monoethyl ether thereof, mixtures thereof of with water, or alternatively pure water.

Particularly preferred diluents are pure water or water/alcohol mixtures, such as, for example, water/methanol or water/ethanol mixtures.

Some reaction steps of the process according to the invention are preferably carried out in the presence of a suitable acid-binding agent. Suitable acid-binding agents are all inorganic and organic bases which can be used customarily. The hydrides, hydroxides, amides, alkoxides, carbonates or hydrogen carbonates of alkali metals, such as, for example, sodium hydride, sodium amide, sodium hydroxide, sodium methoxide, sodium ethoxide, potassium t-butoxide, sodium carbonate or sodium hydrogen carbonate, or alternatively tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU) are preferably used.

Weakly basic inorganic compounds, such as, for example, sodium hydrogen carbonate or sodium acetate, are particularly preferably used.

The final reaction step of the process according to the invention is preferably carried out in the presence of an acidic reaction auxiliary. Acidic reaction auxiliaries which can be used are customary protonic acids or Lewis acids. Inorganic mineral acids, such as hydrochloric acid or sulphuric acid; aliphatic or aromatic carboxylic or sulphonic acids, such as acetic acid, methanesulphonic acid or p-toluene-sulphonic acid; Lewis acids, such as boron trifluoride, iron trichloride, aluminium trichloride or zinc dichloride, or acid ion exchangers are particularly preferably used.

In the last reaction step, hydrochloric acid is particularly preferably used as a reaction auxiliary.

When carrying out the process according to the invention, the reaction temperatures may be varied within a relatively wide range. In general, the reaction is carried out at temperatures of between $-20°$ C. and $+150°$ C., preferably at temperatures of between 0° C. and +120° C.

For carrying out the process according to the invention, 1.0 to 2.0 moles, preferably 1.0 to 1.5 moles, of amine of the formula (III), 1.0 to 1.5 moles, preferably 1.0 to 1.2 moles, of trihalogenomethanesulphenyl chloride of the formula (V) and 1.0 to 1.5 moles, preferably 1.0 to 1.2 moles, of acid-binding agent, furthermore 0.7 to 1.5 moles, preferably 0.9 to 1.2 moles of hydroxylamine hydrochloride and an equivalent amount of an additional acid-binding agent, 0.7 to 1.2 moles, preferably 0.8 to 1.0 moles, of arylhydrazine of the formula (IX) and 1.0 to 10.0 moles, preferably 1.0 to 5.0 moles, of acid reaction auxiliary are generally employed per mole of 3-ketobutyraldehyde dimethyl acetal of the formula (II).

In a preferred embodiment, a procedure is followed in which, initially, the 3-ketobutyraldehyde dimethyl acetal of the formula (II) is stirred for several hours in the temperature range between 10° C. and 30° C. with an appropriate amount of amine of the formula (III) in a suitable diluent, preferably in water, and then an appropriate amount of acid-binding agent, preferably sodium hydrogen carbonate, and then, in the temperature range between −20° C. and +10° C., an appropriate amount of trihalogenomethanesulphenyl chloride is added to the reaction mixture thus obtained. After a short reaction time, this reaction mixture is diluted further; at this point, an alcohol, such as, for example, ethanol, is preferably used as the diluent, an appropriate amount of hydroxylamine hydrochloride and an equivalent amount of acid-binding agent, preferably sodium acetate, are then added, and the reaction mixture is then heated at the boiling point for 1 to 2 hours. The reaction mixture is cooled, the required amount of acid reaction auxiliary, preferably hydrochloric acid and arylhydrazine of the formula (IX), is added, and the mixture is again heated at the boiling point for several hours.

The reaction is carried out and the reaction products are worked up and isolated by generally customary methods, for example by removing the organic diluent, precipitating the reaction product in water, and filtering off with suction and drying the product which can thus be obtained.

Alternative embodiments of the process according to the invention comprise isolation where appropriate of the intermediates of the formula (VI) and/or intermediates of the formula (IV), if appropriate, and further reaction in a separate reaction.

The 4-substituted 3-methyl-1-aryl-5-amino-pyrazoles of the formula (I) which can be prepared with the aid of the process according to the invention are known insecticides (cf. EP No. 201,852).

PREPARATION EXAMPLE

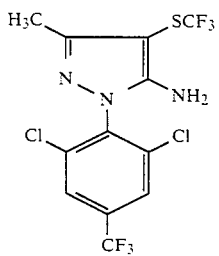

26.5 g (0.2 mol) of 3-ketobutyraldehyde dimethyl acetal and 19 g (0.22 mol) of 53% strength aqueous dimethylamine solution are stirred at room temperature for 16 hours and diluted with 100 ml of water, 18.5 g (0.22 mol) of sodium hydrogen carbonate are added, and the reaction mixture is then cooled to 0° C. At 0° C. to 5° C., 30 g (0.22 mol) of trifluoromethanesulphenyl chloride are passed in in the course of 30 minutes and with cooling, and the mixture is then stirred for a further 30 minutes without cooling, with a gentle stream of nitrogen being passed through the reaction mixture during the course of 15 minutes. 200 g of ethanol, 13 g (0.18 mol) of hydroxylamine hydrochloride and 15 g (0.18 mol) of sodium acetate are then added, the mixture is refluxed for 90 minutes and then cooled to 30° C. to 40° C., 35 g (0.36 mol) of concentrated hydrochloric acid and 42 g (0.17 mol) of 2,6-dichloro-4-trifluoromethylphenylhydrazine are then added, and the mixture is refluxed for a further 16 hours. For working up, 200 g of solvent are distilled off, the resulting suspension is cooled, and the product precipitated is filtered off with suction, washed with 300 ml of water and dried at 50° C. in vacuo.

71 g (91.5% of theory) of 5-amino-3-methyl-1-(2,6-dichloro-4-trifluoro-methylphenyl)-4-trifluoro-methylthio-pyrazole of melting point 146° C.–148° C. are obtained.

It will be appreciated that the instant specification and claims are set forth by way of illustration and not limitation, and that various modifications and changes may be made without departing from the spirit and scope of the present invention.

What is claimed is:

1. A process for the preparation of a 4-substituted 3-methyl-1-aryl-5-amino-pyrazole compound of the formula

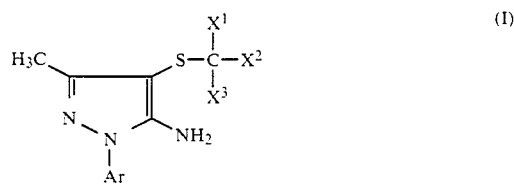

in which
X¹, X² and X³ independently of one another each stand for halogen and
Ar stands for unsubstituted or substituted phenyl, comprising
(a) reacting a 3-ketobutyraldehyde dimethyl acetal of the formula (II)

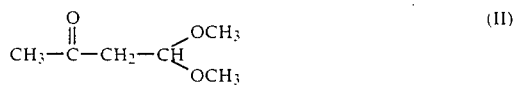

with an amine of the formula (III)

in which
R¹ and R² independently of one another each stand for hydrogen, alkyl, cycloalkyl or for in each case unsubstituted or substituted aralkyl, aryl or heteroaryl, or together with the nitrogen atom to which they are bonded stand for an unsubstituted or substituted heterocyclic ring which contains or does not contain one or more further hetero atoms, (b) reacting the resultant reaction mixture directly without isolation of an intermediate of the formula (IV)

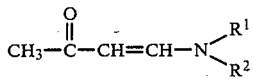  (IV)

in which $R^1$ and $R^2$ have the abovementioned meanings, with a trihalogenomethanesulphenyl chloride of the formula (V)

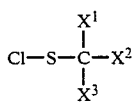  (V)

in which $X^1$, $X^2$ and $X^3$ have the abovementioned meanings, (c) reacting the resultant reaction mixture directly, without isolation of an intermediate of the formula (VI)

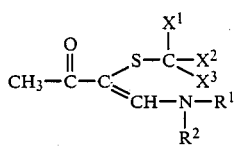  (VI)

in which $R^1$, $R^2$, $X^1$, $X_2$ and $X^3$ have the abovementioned meanings, with hydroxylamine hydrochloride in the presence of an acid-binding agent and (d) reacting the resultant reaction mixture directly with an arylhydrazine of the formula (IX)

  (IX)

in which

Ar has the abovementioned meaning, without isolation of an intermediate of the formula (VII)

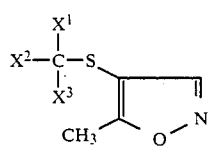  (VII)

which, under the given reaction conditions, immediately react further to give an open-chain tautomer of the formula (VIIIa)

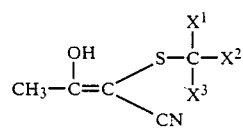  (VIIIa)

in which $X^1$, $X^2$ and $X^3$ have the abovementioned meanings, and an open-chain tautomer of the formula (VIIIb)

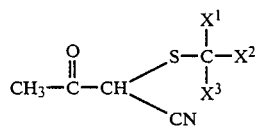  (VIIIb)

in which $X^1$, $X^2$ and $X^3$ have the abovementioned meanings.

2. A process according to claim 1, wherein $X^1$, $X^2$, $X^3$ independently of one another each stand for fluorine, chlorine, bromine or iodine and Ar stands for phenyl which is unsubstituted or monosubstituted or polysubstituted by identical or different substituents, said substituents in each case being: cyano, nitro, halogen, in each case straight-chain or branched alkyl, alkoxy or alkoxycarbonyl, each having 1 to 4 carbon atoms, in each case straight-chain or branched halogenoalkyl or halogenoalkoxy, each having 1 to 4 carbon atoms and 1 to 9 identical or different halogen atoms, or an $-S(O)_n-R^3$ radical, where $R^3$ stands for amino and for in each case straight-chain or branched alkyl, alkylamino, dialkylamino or halogenoalkyl, each having 1 to 4 carbon atoms in the individual alkyl moieties and, in the case of the halogenoalkyl, having 1 to 9 identical or different halogen atoms and n stands for a number 0, 1 or 2.

3. A process according to claim 1, wherein $X^1$, $X^2$ and $X^3$ independently of one another each stand for fluorine, chlorine or bromine and Ar stands for phenyl which is unsubstituted or monosubstituted to pentasubstituted by identical or different substituents, said substituents in each case being: cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or an $-S(O)_n-R^3$ radical, where $R^3$ stands for amino, methylamino, ethylamino, dimethylamino, diethylamino, fluorodichloromethyl, difluoromethyl, tetrafluoroethyl, trifluorochloroethyl, trichloromethyl, trichloroethyl, trifluoromethyl, methyl or ethyl, and n stands for a number 0, 1 or 2.

4. A process according to claim 1, wherein $X^1$, $X^2$ and $X^3$ independently of one another each stand for fluorine or chlorine and Ar stands for phenyl which is unsubstituted or monosubstituted to pentasubstituted by identical or different substituents, said substituents being: fluorine, chlorine, bromine, methyl, ethyl, methoxy, ethoxy, trifluoromethyl, trifluoromethoxy, trifluoromethylthio, trifluoromethylsulphinyl or trifluoromethylsulphonyl.

5. A process according to claim 1, wherein (a) is conducted in the presence of a diluent 6. A process according to claim 1, wherein (b) is conducted in the presence of a diluent.

7. A process according to claim 1, wherein (b) is conducted in the presence of an acid binding agent.

8. A process according to claim 1, wherein (c) is conducted in the presence of an acid binding agent.

9. A process according to claim 1, wherein (d) is conducted in the presence of a diluent.

10. A process according to claim 1, wherein (d) is conducted in the presence of an acid reaction auxiliary.

11. A process according to claim 1, wherein one or more of (a), (b), (c) and (d) are conducted in tne presence of a diluent and wherein the diluent is selected from the group consisting of an inorganic diluent, water, a mixture of an inorganic diluent and water.

12. A process according to claim 1, wherein one or more of (a), (b), (c) and (d) are conducted in the presence of a diluent and wherein the diluent is selected from the group consisting of an aliphatic hydrocarbon, a halogenated aiiphatic hydrocarbon, an alicyclic hydrocarbon, a halogenated aliphatic hydrocarbon, an aromatic and a halogenated aromatic.

13. A process according to claim 12, wherein said diluent is a mixture with water.

14. A process according to claim 1, wherein one or more of (a), (b), (c) and (d) are conducted in the presence of a diluent and wherein the diluent is selected from the group consisting of ethers, amides, esters, sulphoxides and alcohol.

15. A process according to claim 14, wherein said diluent is in a mixture with water.

16. A process according to claim 15, wherein the diluent is a mixture of alcohol and water.

17. A process according to claim 1, wherein (d) is carried out in the presence of an acidic reaction auxiliary selected from the group consisting of inorganic mineral acides, aliphatic carboxylic acids, aromatic carboxylic acids, sulphonic acids and Lewis acids and acid ion exchangers.

18. A process according to claim 1, wherein (d) is conducted in the presence of an acidic reaction auxiliary selected from the group consisting of hydrocholoric acid, sulphuric acid, acetic acid, methanesulphonic acid, p-toluenesulphonic acid, boron trifluoride, iron trichloride, aluminum trichloride and zinc dichloride.

19. A process according to claim 1, wherein the reaction is carried out at temperature of between 0° C. and 120° C.

20. A process according to claim 1, wherein per mole of 3-ketobutyraldehyde there is employed 1.0 to 2.0 moles of the amine, 1.0 to 1.2 moles of the trihalogenomethane sulphenyl chloride, 0.7 to 1.5 moles of the hydroxylamine hydrochloride and 0.8 to 1.0 moles of the arylhydrazine.

* * * * *